(12) United States Patent
Inoue et al.

(10) Patent No.: US 6,546,282 B1
(45) Date of Patent: Apr. 8, 2003

(54) DEVICE FOR IONTOPHORESIS

(75) Inventors: Kazutaka Inoue, Tsukuba (JP); Hirotoshi Adachi, Tsukuba (JP); Hiroyuki Maeda, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/556,174

(22) Filed: Apr. 20, 2000

(30) Foreign Application Priority Data

Apr. 23, 1999 (JP) ............................................ 11-115993

(51) Int. Cl.[7] .................................................. A61N 1/30
(52) U.S. Cl. ........................................ 604/20; 424/449
(58) Field of Search ............................ 604/20; 424/448, 424/449

(56) References Cited

U.S. PATENT DOCUMENTS 5,006,108 A * 4/1991 LaPrade ...................... 604/20
5,010,896 A * 4/1991 Westbrook .................. 607/148

* cited by examiner

*Primary Examiner*—Edward K. Look
*Assistant Examiner*—Dwayne J. White
(74) *Attorney, Agent, or Firm*—Townsend & Banta

(57) ABSTRACT

A handling-convenient device for iontophoresis, which can supply spotted regions suffering from disease with a proper quantity of current at the same time. The device for iontophoresis includes a power source apparatus having a plurality of output terminals outputting currents of predetermined values adjusted by a plurality of current control circuits, respectively, and a plurality of connecting cords, each cord being connected with one of the output terminals of the power source apparatus at one end thereof and being connected with an electrode structure at the other end. The connecting cords are attached with the power source apparatus in a mutually attachable/detachable fashion via connection terminals. The power source apparatus has an LED located thereon to notify of the energization status of the device and a power switch externally located thereon to control starts and stops of the apparatus.

13 Claims, 7 Drawing Sheets

Fig. 3
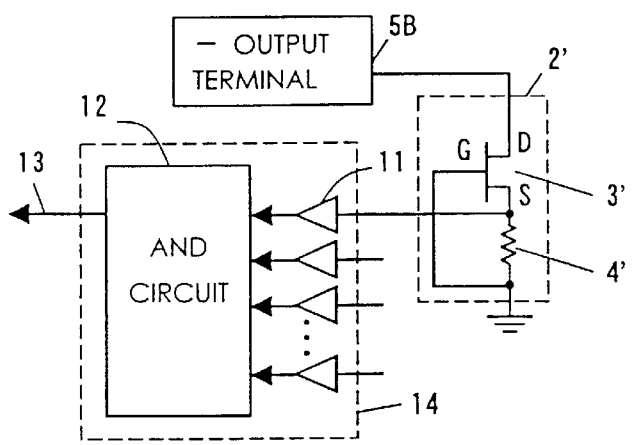
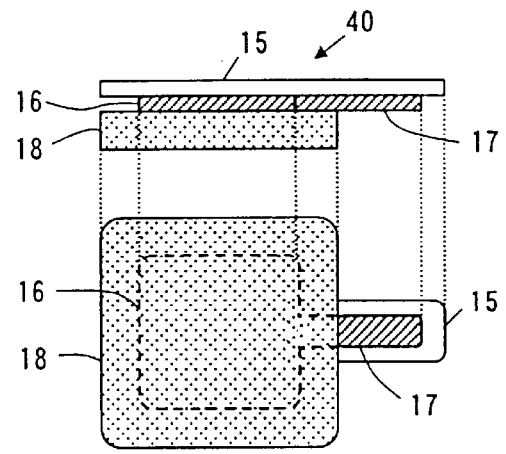
Fig. 4A
Fig. 4B
Fig. 5
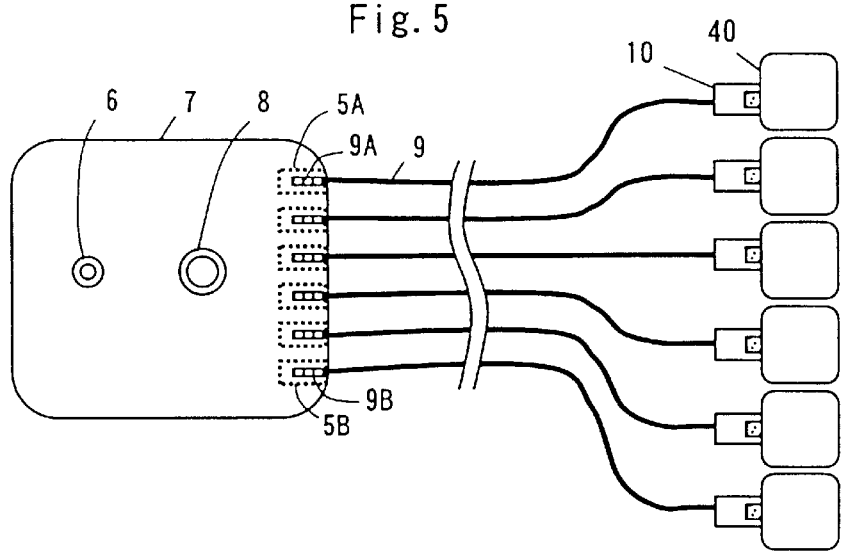

DEVICE FOR IONTOPHORESIS

BACKGROUND OF THE INVENTION

The present invention relates to a device for iontophoresis to be applied through skin or mucous, and in particular, relates to a device for iontophoresis for administering appropriate quantity of drug at respective spotted regions to be treated.

Iontophoresis is percutaneous absorption enhancing system using electricity as external stimulation, and its principle is that barrier penetration through skin by drug molecules is enhanced mainly by energization, that is, based on a force to move positively charged molecules from a positive electrode to a negative electrode and to move negatively charged molecules from the negative electrode to the positive electrode, in an electric field generated between the positive electrode and a negative electrode. (Refer to Journal of Controlled Release, Vol. 18, 1992, pp. 213–220; Advanced Drug Delivery Review, Vol. 9, 1992, p. 119; Pharmaceutical Research, Vol. 3, 1986, pp. 318–326)

A conventional iontophoresis device has such a problem that quantity of dosage is different and skin is irritated due to individual difference in impedance in the region to be applied, but in recent years, a constant current apparatus is used so that a predetermined level of current is maintained despite of such a difference in impedance.

The constant current apparatus, which takes it advantage that delivery speed of a drug and current quantity are correlated, is capable of maintaining drug delivery speed at a constant, not based on impedance due to individual difference. In addition, since as for skin irritation an approximate current density not more than 0.2 mA/cm$^2$ is considered to be low-irritating in general, the current quantity (formulation area×maximum current density≧predetermined current quantity) to be obtained from an area of formulation (an electrode structure) applied to skin and a maximum current density, being set at not more than 0.2 mA/cm$^2$ serves to give rise to an effect that safetiness is maintained.

However, when an applicable area covers a wide range, currents do not always flow in an homogeneous fashion based on status of locations to be treated, in the above described constant current apparatus, either, and in some cases, heterogeneity in current may be occurred. In such cases, sufficient drug dosage is not implemented at a part of the region to be treated, and moreover, overdosage of a drug takes place at the other part of the region to be treated, in a result, high current density could cause inconveniences such as skin burning, etc.

As a device to dissolve these problems, Japanese Patent Laid-Open No. 61-100264 specification, for example, discloses an applicator having means for supplying constant current to a plurality of drug containing means and respective containers, and in addition, National Publication of International Patent Application No. 7-507951 specification discloses a device including a current-Miller circuit comprising a plurality of electrode segments each of which contains a constant-current source, and a circuit thereof. The prior art divides an applicable region into a plurality of parts and supplies an equal current to each divided applicable region so that dispersion of current density at the applicable region is made to be a minimum.

SUMMARY OF THE INVENTION

However, the prior art discloses nothing about supplying the spotted regions to be treated with proper currents (that is, drugs) simultaneously in case of local treatment for which iontophoresis device may be frequently used. For example, by using a handling-convenient device in the case where there exist spotted regions suffering from herpes zaster and urticaria, etc., each region to be treated could be supplied with a proper current (that is, drug) at the same time, and thus its resulting therapeutic efficiency is expected to be remarkably improved, but such a device is conventionally not yet known.

It is, therefore, an object of the present invention to provide a handling-convenient device for iontophoresis which can supply a proper quantity of current each spotted region suffering from disease at the same time.

The present inventors have been earnestly and repeatedly exerting themselves on researches to attain the object, and consequently, have enabled various spotted regions to be treated to have a desired quantity of drug dosage by connecting a plurality of connecting cords with respective output terminals of a power source apparatus having a plurality of current control circuits supplying predetermined currents, and thereby, have found out that drugs can be dosed at a high bioavailability through skin with good repeatability, and reached the present invention.

The device for iontophoresis according to the present invention comprises a power source apparatus having a plurality of output terminals outputting currents of the predetermined values adjusted by a plurality of current control circuits, respectively, and a plurality of connecting cords, each cord being connected with one of the output terminals of the power source apparatus at one end thereof and being connected with an electrode structure at the other end. Here one end of a connecting cord may be formed in an attachable/detachable fashion with output terminals of the power source apparatus. This way, connecting cords can be connected in accordance with a number of applicable portions of the electrode structures, and unnecessary connecting cords can be detached.

In addition, another device for iontophoresis according to the present invention comprises a power source apparatus having a plurality of output terminals outputting currents of the predetermined values adjusted by a plurality of current control circuits, respectively, and a connecting cord portion having a base coupled to the power source apparatus in an attachable/detachable fashion, a plurality of input terminals disposed on the base corresponding to each of the output terminals of the power source apparatus and a plurality of connecting cords, each cord being connected with one of the output terminals of the power source apparatus at one end thereof and being connected with an electrode structure at the other end. Thus, the power source apparatus and connecting cord parts are mutually made attachable/detachable so that one of those parts can be replaced based on the necessity. In addition, one end of a connecting cord may be formed to be attachable/detachable with the input terminals on the base.

The power source apparatus may includes a voltage adjusting circuit to adjust an output voltage in accordance with an output current value. Such an arrangement can serve to keep the output voltage at a voltage which is required and minimum value to maintain a constant current. In addition, with the power source apparatus itself being adjusted, or with connection relationships among connecting cords, the electrode structure, and the output terminals of the power source apparatus being altered, predetermined current values of respective electrode structures can be made variable in accordance with a plurality of regions suffering from diseases and area suffering from diseases. Moreover, the other ends of the connecting cords are formed so as to be attachable/detachable with the electrode structure.

With the configuration described above, a handling-convenient device for iontophoresis can be obtained which can supply a good quantity of current for each spotted portion suffering from disease, at the same time is available.

BRIEF DESCRIPTION OF THE DRAWINGS

FIG. 3 is a circuit diagram showing an example in the case where a voltage adjusting circuit is added to a current control circuit connected with an output terminal of a negative electrode side;

FIG. 4A is a conceptual side view showing an example of an electrode structure connected with a connecting terminal of the device of the present invention, and FIG. 4B is a bottom view thereof;

FIG. 5 is a general view showing an example at the time when an electrode structure is connected with the present device;

DESCRIPTION OF THE PREFERRED EMBODIMENTS

The present invention will be described in detail with reference to the drawings.

Figure 1:
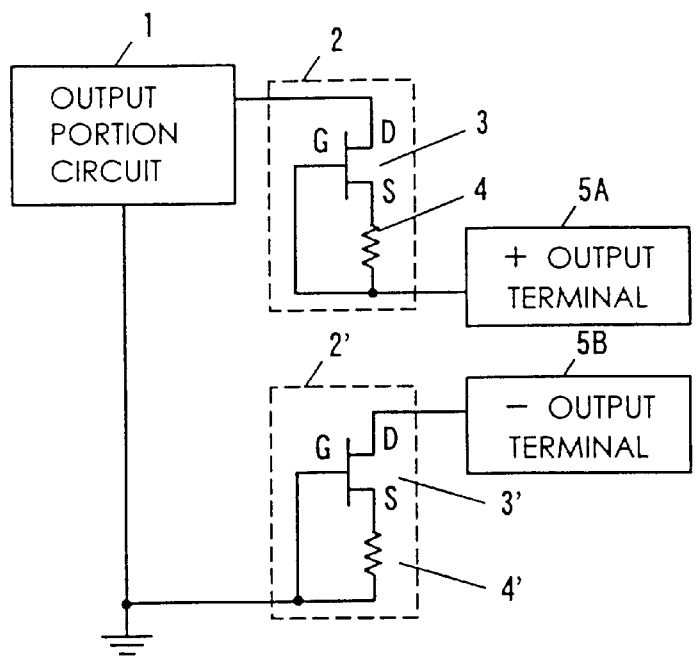
FIG. 1 is a diagram showing a part of a circuit of a power source apparatus used for a device for iontophoresis according to the present invention.

FIG. 1 is a diagram showing a part of a circuit of a power source apparatus used for a device for iontophoresis according to the present invention. The power source apparatus of the present device has a plurality of the circuits and is formed so as to be capable of supplying a constant current quantity to each region suffering from diseases. The present circuit as shown in the drawing comprises an output portion circuit 1, a positive electrode side output terminal 5A, a negative electrode side terminal 5B, and current control circuits 2 and 2' positioned between the output portion circuit 1 and the positive electrode side output terminal 5A or a negative electrode side terminal 5B. The drawing shows both of the current control circuits respectively provided to the positive side and the negative side, but in an actual circuit, one of the current control circuits 2 and 2' is used.

The output portion circuit 1 comprises a generally used battery, a booster circuit, a power switch, an LED (light emission diode) and an output control circuit, etc, although each of which is not shown in the drawing.

The current control circuits 2 and 2' comprise field effect transistors 3 and 3', and fixed resistors 4 and 4', respectively. In the current control circuit 2, a drain D of the field effect transistor 3 is connected with the output portion circuit 1, and a source S is connected with a gate G via a fixed resistor 4 and a connecting portion between the gate G and the fixed resistor 4 is connected with the positive electrode side output terminal 5A. In addition, in the current control circuit 2', a drain D of the electric field effect transistor 3' is connected with the negative electrode side output terminal 5B, and a source S is connected with a gate G via a fixed resistor 4' and a connecting portion between the gate G and the fixed resistor 4 is connected with the output portion circuit 1. The current control circuits 2 and 2', which are configured so that voltages between the gates G and the sources S of the field effect transistors 3 and 3' are adjusted by currents flowing through the fixed resistors 4 and 4', operate as constant current circuits to implement constant current control. This current control circuit, which is a simple and easy circuit using a field effect transistor and a fixed resistor, does not need any feedback signals for current control (that is, being self-feedback) and thus is capable of comprising by any of the positive electrode side and the negative electrode side. A position where an output terminal corresponding with this current control circuit is disposed, is at the positive electrode side when a drug is a cationic drug, or is at the negative electrode side when a drug is an anionic drug.

Figure 2:
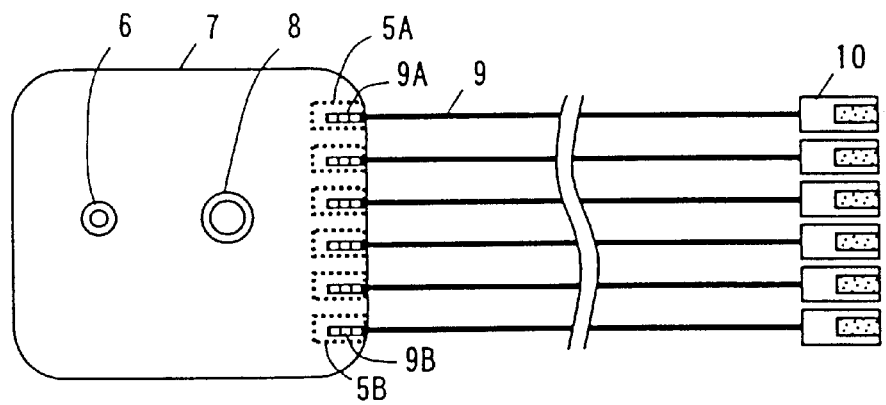
FIG. 2 is a top view showing an example of a device for iontophoresis according to the present invention.

FIG. 2 is a top view showing an example of a device for iontophoresis according to the present invention. The device comprises, as shown in the drawing, a power source apparatus 7 in which a plurality of circuits shown in FIG. 1 are built in, and a plurality of connecting cords 9 provided corresponding to each circuit. The power source apparatus 7 is provided with an LED 6 being an indicator to notify its energization status outward, and a power switch 8 to control starts and stops of the device from outside, being disposed on the top thereof. In addition, one end of a connecting cord 9 is connected with an output terminal 5A or 5B of the power source apparatus 7 and the other end thereof is connected with the later-described electrode structure via a connection terminal 10. Here, one end of the connecting cord 9 may be connected fixedly with the output terminal 5A or 5B, and may be attachable/detachable using connection terminals 9A and 9B provided at one end of the connecting cord 9 as shown in the drawing. In the drawing, the four output terminals between the positive electrode side output terminal 5A and the negative electrode side output terminal 5B are respectively used as positive electrode side output terminals or as negative electrode output side terminals at need. Material for the connecting cord 9 is not limited in particular, but is preferably one having flexibility so that the electrode structure may be disposed freely at the part where it is applied.

Thus, in the device of the present invention, the power source apparatus 7 is provided with a plurality of current control circuits 2 or 2' and connecting cords 9 are attached with a plurality of output terminals 5A corresponding herewith so that a proper drug can be supplied toward spotted region to be treated at the same time by simple and easy means, with fixed current control. In addition, the fixed resistors 4 and 4' provided at each current control circuit are arranged to have different resistor values so that different output currents may be predetermined for each output terminal. In this case, a variable resistor may be used instead of the fixed resistors 4 and 4'. A fixed resistor being replaced with a variable resistor will serve to enable variation of the predetermined values due to dispersion of components to be adjustable.

FIG. 3 is a circuit diagram showing an example in which a voltage adjusting circuit 14 is added to a current control circuit 2' connected with a negative electrode side output terminal 5B. The voltage adjusting circuit 14, which is for generating a feedback signal 13 to keep a minimum voltage necessary to maintain a fixed current, comprises a plurality of voltage comparators 11 and AND circuits 12. The circuit 14, which is provided at the side of the current control circuit 2' as shown in the drawing, may be provided at the side of the current control circuit 2.

In the case where fixed current control is implemented via a plurality of output terminals as in the present device, feedback signals are obtained from a plurality of circuits detecting currents, respectively. Then, the voltage adjusting circuit 14 gathers feedback signals together into one, and thus output voltages become controllable with the feedback signal from a current detecting circuit. The voltage adjusting circuit 14 notifies to the output portion circuit 1 with a feedback signal 13 that the current control circuits 2' connected with the respective output terminals have reached the predetermined current values. Therefore the output voltages can be adjusted into a necessary and minimum voltage, and the power saving for the circuit can be achieved with a fixed current control.

Operation of the voltage adjusting circuit 14 firstly starts with checking the voltage comparator 11 whether or not the output current flowing to the fixed resistor 4' reached a predetermined value. The voltage comparator 11 is a comparator circuit, which outputs an "H" signal when the output current reaches a predetermined value, and outputs an "L" signal when the output current does not reach a predetermined value, and an output signal thereof is transmitted to an AND circuit 12. The AND circuit 12, which is a logical product circuit having multi-inputs, outputs and "H" signal when all output currents flowing through the output terminals reach a predetermined value, and outputs an"L" signal when any one of output currents does not reach a predetermined value. The generated output signal of the AND circuit 12 is transmitted to the output portion circuit 1 as a feedback signal 13. The output portion circuit 1 decreases the output voltage when the feedback signal 13 is an "H" and increases the output voltage when the output signal is an "L" so that the output voltage is adjusted.

The present device comprises such voltage adjusting means so as to be able to suppress power consumption of an battery and to become available for use for longer period or for many times.

FIG. 4A is a conceptual side view showing an example of an electrode structure 40 that is connected with a connection terminal 10 of the device, and FIG. 4B is a bottom view thereof. In addition, FIG. 5 is an overall view showing an example of an electrode structure 40 that is connected with the device. The electrode structure 40 used in the present invention, is not limited in particular if it is an electrode normally used for a device for iontophoresis. It preferably comprises a non-conductive support 15, an electrodes 16 and an electrode terminal 17 located on the support 15, and a gel layer 18 located on the support 15 so as to cover the electrode 16. The gel layer 18 that is made with hydrophilic polymers containing drugs or electrolytes is used.

As materials for the electrode 16 of the electrode structure, silver, carbon, aluminum, zinc, copper, or iron, etc., are preferably used for a positive electrode. Among them, silver has good electric characteristics such as resistance value, etc., and can be made low costly with a high productivity if silver paste is used. In addition, as materials for a negative electrode, silver/silver chloride is suitably and preferably used, but every metal material can be used if no corrosion, etc. takes place during a period when it is stored.

As a base material for the gel layer 18, for example, polyacrylic acid, sodium polyacrylic acid, methacrylic acid, polyacrylamide, polyvinyl pyrrolidone, polyvinyl alcohol, carboxymethyl cellulose, sodium alginate, dextran, karaya gum, gum arabic, gelatin, agar, etc., are used.

Figure 6:
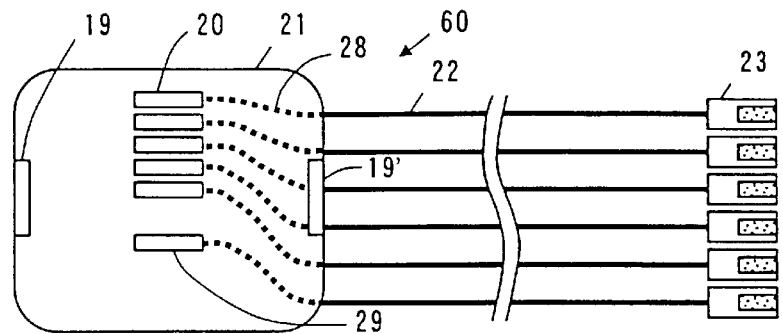
FIG. 6 is a conceptual view showing an example of connecting cords used for another device for iontophoresis according to the present invention.
Figure 7:
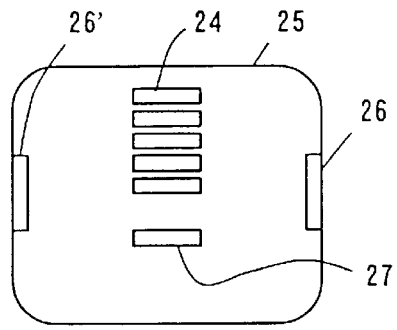
FIG. 7 is a bottom view showing an example of a power source apparatus attachable/detachable with connecting cord parts.

FIG. 6 is a conceptual view showing an example of a connecting cord used for another device for iontophoresis according to the present invention. A power source apparatus is attached to the connecting cord portion of the example in an attachable/detachable fashion. FIG. 7 is a bottom view showing the example of the power source apparatus.

The connecting cord portion 60 comprises a base 21 and a plurality of connecting cords 22 as shown in FIG. 6. Here, the base 21 comprises input terminals 20 and 29 connected with output terminals of the later described power source apparatus placed on one surface, and an internal wiring 28 so as to connect with a connecting cord 22 on one side surface of the base. The internal wiring 28 may be provided separately from the connecting cord 22 as in the example, but the connecting cord 22 may be extended so as to connect with the input terminal 20. One end of the connecting cord 22 may be formed so as to be attachable/detachable with the base 21 by means of a connector, etc., which is not shown, and thereby the cords corresponding with regions suffering from disease are attached, so that one or more excessive cords can be omitted. The connecting cord 22 has a connecting terminal 23 at the other end thereof to be connected with the electrode structure.

A power source apparatus 25 comprises, as shown in FIG. 7, output terminals 24 and 27 that are exposed on the bottom surface of the device. Here, the output terminal 24 is an output terminal at a drug side for supplying a current to the electrode structure containing the drug, and the output terminal 27 is an output terminal at an electrolyte side for supplying a current to the electrode structure containing the electrolyte. In addition, the power source apparatus 25 is provided with connecting parts 26 and 26' to be engaged with connecting parts 19 and 19' of the connecting cord portion 60. Thus, the power source apparatus 25 will become easily attachable/detachable with the connecting cord portion 60.

In addition, the way how to connect the output terminal 24 provided in the power source apparatus 25 with the input terminal 20 in the connecting cord portion 60 is changed, and by connecting a plurality of output terminals 24 with one input terminal 20 a value of output current from the connecting terminal 23 can be made variable. Moreover, by connecting a plurality of outputs from output terminal 24 with one connecting cord 22, a value of output current from the connecting terminal 23 can be made variable. Thus, the connecting cord portion 60 not only connects an output terminal 24 with the electrode structure 40 provided in the power source apparatus 25, but also is easily able to make the predetermined current value for each electrode structure variable by altering the connection relationship between an output terminal 24 and an input terminal 20 or between a connection terminal 23 and a connecting cord 22.

As described above, an iontophoresis according to the present invention is a useful device especially for a patient who has regions to which drug is applied and which are spotted there locally. For example, in the case where a patient suffers from spotted and locally-existed diseases such as herpes zoster or urticaria, or in the case where there are regions such as fingers and limbs which are shaped largely curbed and are difficult to be taped up, electrode structures are attached to each connecting cord of the device so as to become easily applicable. In addition, the electrode structure containing drug is attachable/detachable with the connecting cord, and its size can be changed so as to comply with sizes of regions to be applied or finger sizes. In addition, since the connecting cord can be detached from the power source apparatus or the base of the connecting cord portion, it does not have to be concerned about the unnecessary addition of electrode structures, and it is a device excellent in terms of economy or productivity.

Moreover, the device also can predetermine any current value optionally for each region to be treated. The change of the predetermined current value is made by changing values of circuit elements inside the power source apparatus or adjusting internal connections, or by changing connection relationship between connecting cords and an output terminal of the power source apparatus. In addition, a device, into which a power source apparatus without using connecting cords and an electrode structure are integrated, can be used where an region suffering from a disease is concentrated in one spot. In the device, the predetermined current value is adjusted by changing width or length of the electrode terminal of the electrode structure, and by altering the connection relationship between a plurality of output terminals in the power source apparatus and an electrode terminal of the electrode structure to be connected therewith. Thus, also even when respective regions to be treated has different application areas, a fixed current density can be supplied to respective application region. This is useful when necessary drug dosage is different in regions suffering from diseases, or the like.

EXAMPLE 1

Figure 8:
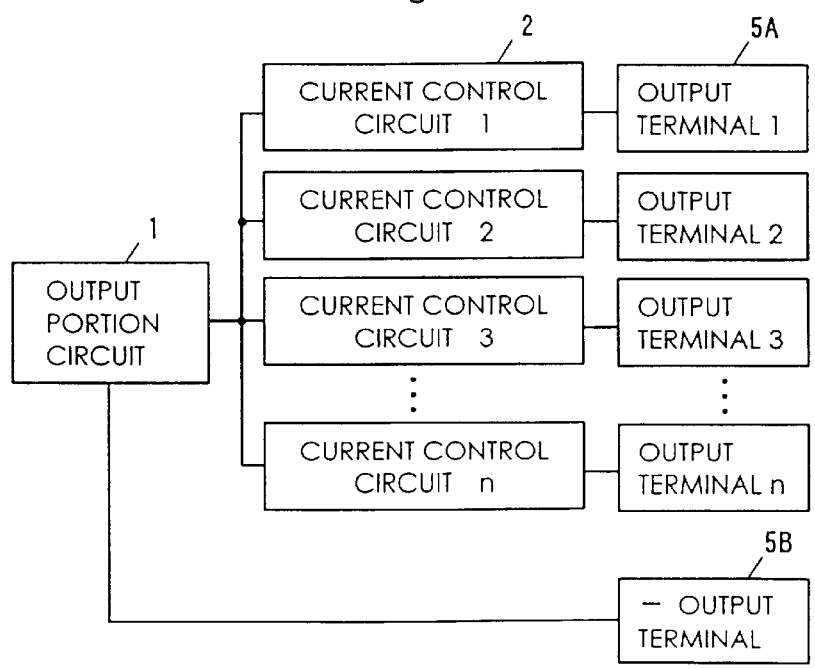
FIG. 8 is a circuit block diagram in which current control circuits and output terminals are connected with an output portion circuit.

FIG. 8 is a circuit block diagram when current control circuits 2 and output terminals 5A and 5B are connected with an output portion circuit 1 used in an iontophoresis device. Here, the predetermined current value for respective current control circuits 2 was 0.2 mA.

Comparative Example 1

Figure 9:
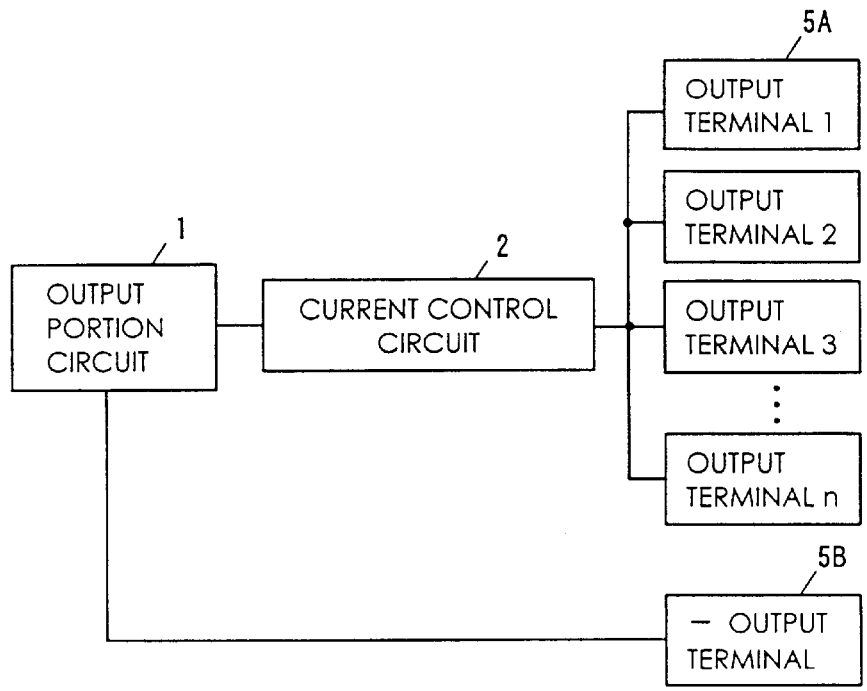
FIG. 9 is a circuit block diagram showing the case where a single current control circuit and output terminals are connected with an output portion circuit.

FIG. 9 is a circuit block diagram when a single current control circuit 2 and output terminals 5A and 5B are connected with an output portion circuit 1 used in an iontophoresis device. Here, the predetermined current value for the current control circuit 2 was 1 mA.

Test Example 1

In circuits for Example 1 and Comparative Example 1, output currents (mA) for each load resistance (kΩ) were measured when the number of output terminals was set to 5 (n=5), and the output voltages were set to 5 V and 10 V. Results thereof are indicated in Table 1 and Table 2. Here, measured currents 1 are values of output currents (mA) for respective output voltages (V) in Example 1, and measured currents 2 are values of output currents (mA) for respective output voltages (V) in Comparative Example 1.

TABLE 1

| Output voltage (V) | Load resistance (kΩ) | Measured current 1 (mA) | Measured current 2 (mA) |
| --- | --- | --- | --- |
| 5 V | 10 kΩ | 0.2 mA | 0.44 mA |
| 5 V | 20 kΩ | 0.2 mA | 0.22 mA |
| 5 V | 30 kΩ | 0.13 mA | 0.15 mA |
| 5 V | 40 kΩ | 0.1 mA | 0.11 mA |
| 5 V | 50 kΩ | 0.08 mA | 0.09 mA |

TABLE 2

| Output voltage (V) | Load resistance (kΩ) | Measured current 1 (mA) | Measured current 2 (mA) |
| --- | --- | --- | --- |
| 10 V | 10 kΩ | 0.2 mA | 0.44 mA |
| 10 V | 20 kΩ | 0.2 mA | 0.22 mA |
| 10 V | 30 kΩ | 0.2 mA | 0.15 mA |
| 10 V | 40 kΩ | 0.2 mA | 0.11 mA |
| 10 V | 50 kΩ | 0.18 mA | 0.09 mA |

(Result 1)

As shown in Table 1 and Table 2, Example 1 (measured current 1) had less variable current values for each load resistance in any voltage value as compared with Comparative Example 1 (measured current 2), and especially, when the output voltage was 10 V, its effect was great. In addition, when load variation was remarkable, necessity of corresponding output voltages with high load resistance implies usefulness of a voltage adjusting circuit to adjust output voltages in accordance with loads.

Test Example 2

In the iontophoresis device of Example 1 and Comparative Example 1, the output performance in the case where one electrode structure contains local anesthetic, was assessed by means of pharmacological effects. In the present Test Example, as an electrode structure containing drug, a hydrophilic polymer gel, in which 4% (w/w) of lidocaine hydrochloride, 0.01% (w/w) of epinephrine, 1.5% (w/w) of agar, and 94.49% (w/w) of purified water were contained, was used.

In the present Test Example, the effects of anesthesia were compared when one of the plurality of electrode structures containing one kind of drug was applied thereto. Firstly, prior to starting of a test, guinea pigs were subjected to depilation with hair clippers and an electric shaver, and skin surfaces thereof were wiped off well with a piece of gauze which had been dipped in hypothermal water. A right or left portion of the midlines of their backs being center lines was stimulated with a irritating needle so as to determine region where skin deflation reflex revealed for certain being region to be applied by the hydrophilic polymer gel, and an electrode structure containing sodium chloride were applied onto the other region subjected to depilation. The electrode structure (6 cm$^2$) containing drug was connected to the positive electrode side and the electrode structure (6 cm$^2$) containing sodium chloride was connected to the negative electrode side, respectively, and the energization was started. The energization condition was set that a direct current 0.1 mA/cm$^2$ is applied to the electrode structure containing drug during 15 minutes. After completion of energization, the region where the electrode structure containing drug was applied, was subjected to irritation with irritating needles six times so that changes in skin deflation reflex were chronologically scored with six stages. The scores express the times of deflation reflex (or felt irritation) of skins of guinea pigs, as shown as follows:

Score 0: No irritation is felt for six times.
Score 1: Irritation is felt only once.
Score 2: Irritation is felt twice.
Score 3: Irritation is felt for three times.
Score 4: Irritation is felt for four times.
Score 5: Irritation is felt for five times.
Score 6: Irritation is felt for six times.

(But, since skins of guinea pigs are not so good in terms of adhesiveness, dispersion in data may take place.)

(Result 2)

Figure 10:
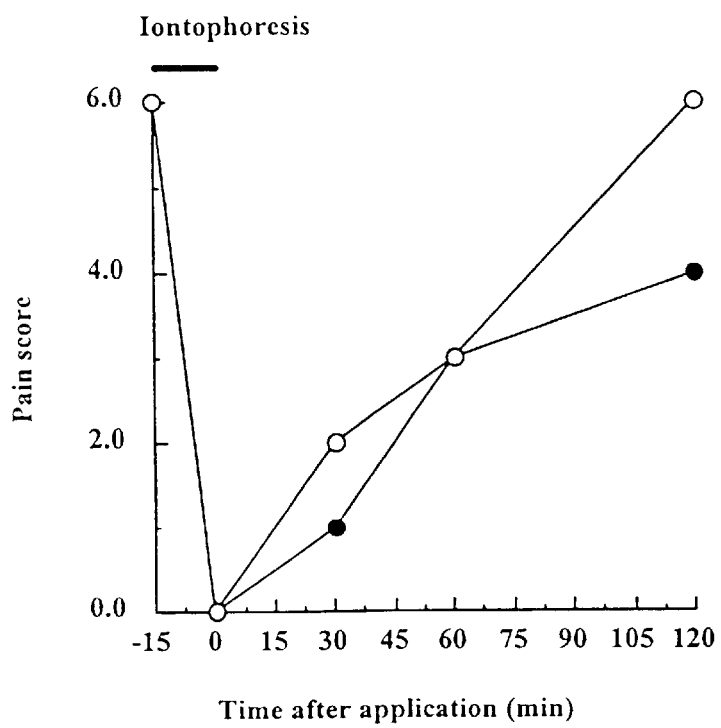
FIG. 10 is a graph showing pain scores in Test Example 2.

FIG. 10 is a graph showing a result for Test Example 2. The horizontal axis in the graph shows time period (in minute) after iontophoresis is applied, and the vertical axis shows pain scores (graphs to be described hereafter will be likewise). In the present graph, the symbol "●" indicates score status in Example 1, and the symbol "○" indicates score status in Comparative Example 1, respectively. As shown in the graph, painlessness scoring zero for the both cases was obtained immediately after completion of energization in Example 1 and Comparative Example 1. In addition, thereafter, the effect of anesthesia decreased gradually, after approximately 120 minutes, a normal status (no anesthesia) of Score 6 or a similar status came back. The device in Example 1 implies that an output from at least one of terminals thereof can be set optionally.

Test Example 3

With the same method as in Test Example 2, using the iontophoresis device comprised as in Example 1 and in Comparative Example 1, the effects of anesthesia were compared when five electrode structures containing drug were applied to back skins of normal guinea pigs.

(Result 3)

Figure 11A:
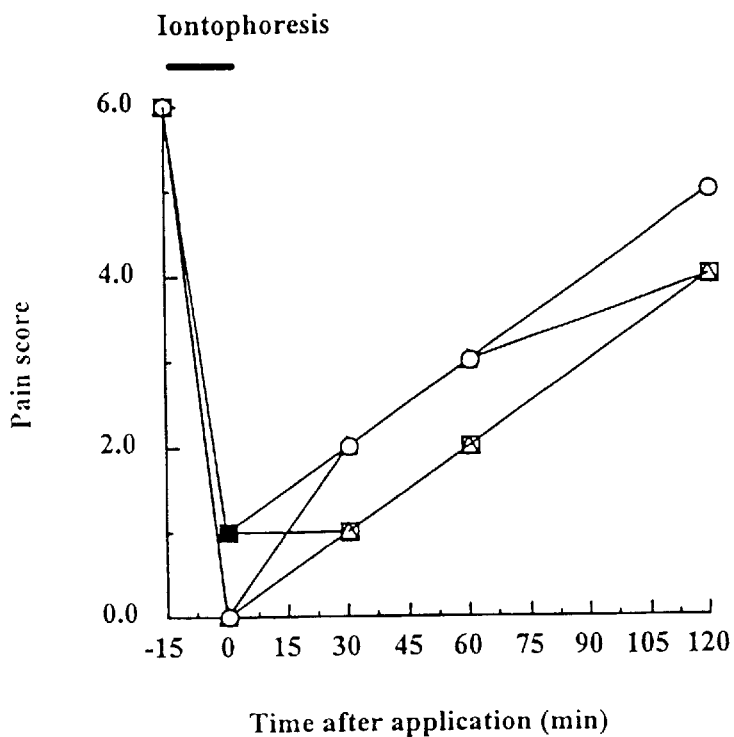
FIG. 11A is a graph for Example 1 showing pain scores in Test Example 3.
Figure 11B:
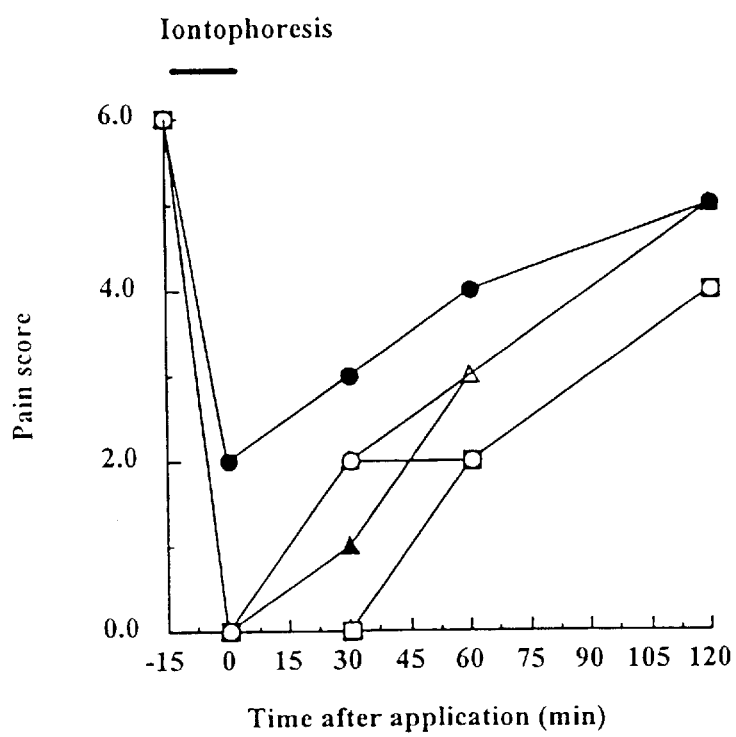
FIG. 11B is a graph for Comparative Example 1 thereon.

FIG. 11A is a graph showing a result for Test Example 3 on Example 1, and FIG. 11B is a graph on Comparative Example 1. In the present graph, the symbol "○" indicates score status of normal skins (electrode structure 1), the symbol "●" indicates score status of normal skins (electrode structure 2), the symbol "Δ" A indicates score status of normal skins (electrode structure 3), the symbol "▲" indicates score status of normal skins (electrode structure 4), and the symbol "□" indicates score status of normal skins (electrodestructure 5),respectively. As shown in the graph, painlessness was almost obtained immediately after completion of energization in Example 1 and Comparative Example 1, and thereafter, anesthesia decreased gradually. However, Comparative Example 1 was observed to tend to show greater dispersion compared with Example 1. Thus, it was implied that all outputs from output terminals can be controlled simultaneously by the present invention.

Test Example 4

With the same method as in Test Example 2, using the iontophoresis device comprised as in Example 1 and in Comparative Example 1, four among the five electrode structures containing drug were applied to back skins of normal guinea pigs, the remaining one was applied to an injured skin, and then anesthesia were compared. The injured skin was subjected to tape stripping five times.

(Result 4)

Figure 12A:
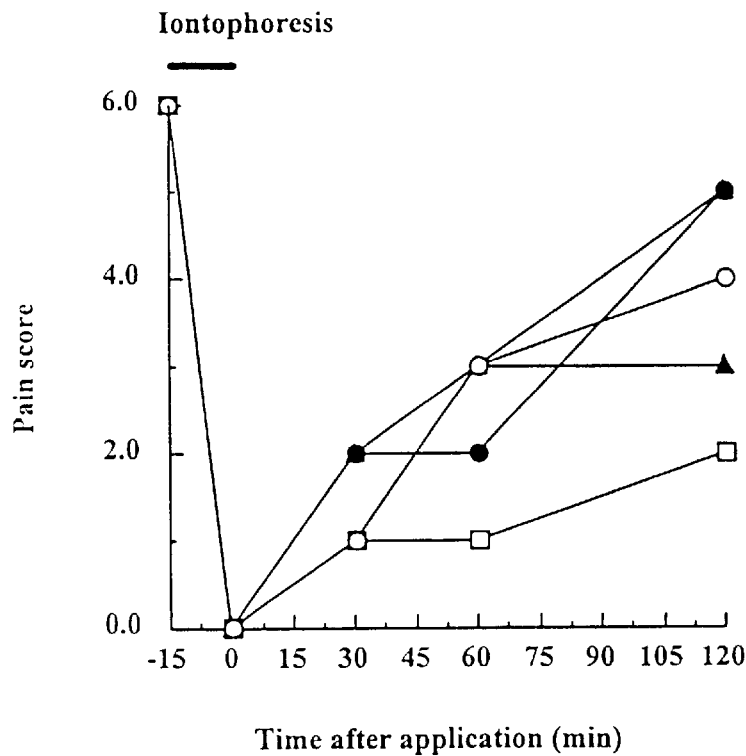
FIG. 12A is a graph for Example 1 showing pain scores in Test Example 4.
Figure 12B:
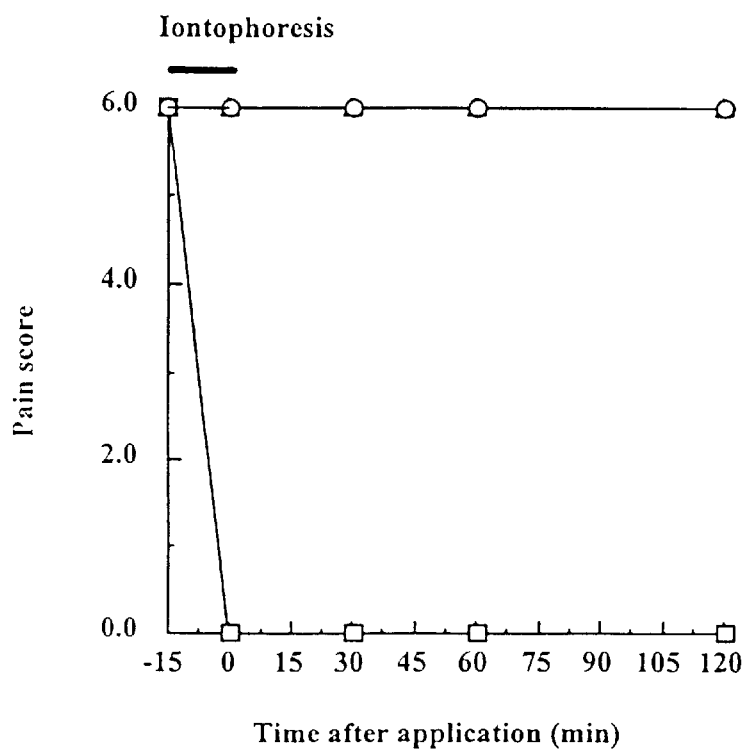
FIG. 12B is a graph for Comparative Example 1 thereon.

FIG. 12A is a graph showing a result for Test Example 4 on Example 1, and FIG. 12B is a graph on Comparative Example 1. In the present graph, the symbol "○" indicates score status of normal skins (electrode structure 1), the symbol "●" indicates score status of normal skins (electrode structure 2), the symbol "Δ" indicates score status of normal skins (electrode structure 3), the symbol "▲" indicates score status of normal skins (electrode structure 4), and the symbol "□" indicates score status of an injured skin (electrode structure 5), respectively. As shown in the graph, in Comparison Example 1, anesthesia was observed only at the injured region. On the other hand, in Example 1 painlessness was obtained in all regions immediately after completion of energization, and thereafter, anesthesia decreased gradually.

Since not all skins at regions for application have the same impedance, in the case where extremely badly injured skins coexist as in Example 1 as well, it is useful to be able to make the energizaiton homogeneous. In addition, in Comparative Example 1, a burning was identified due to current concentration into the region where the effect anesthesia was observed. That is, the device in Example 1 was also excellent in safety.

Test Example 5

Using the iontophoresis device comprised as in Embodiment 1 and in Comparative Example 1, five electrode structures containing drug were applied to back skins of guinea pigs, skins of which were under all mutually different injured conditions, and then anesthesia were compared. The differently injured skins were produced by implementing tape stripping 0, 1, 2, 3, and 5 times.

(Result 5)

Figure 13A:
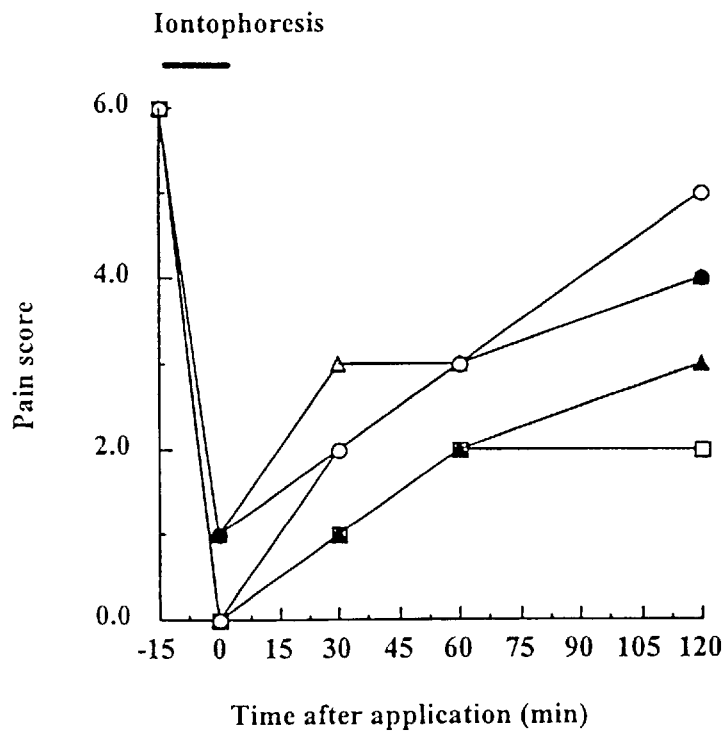
FIG. 13A is a graph for Example 1 showing pain scores in Test Example 5.
Figure 13B:
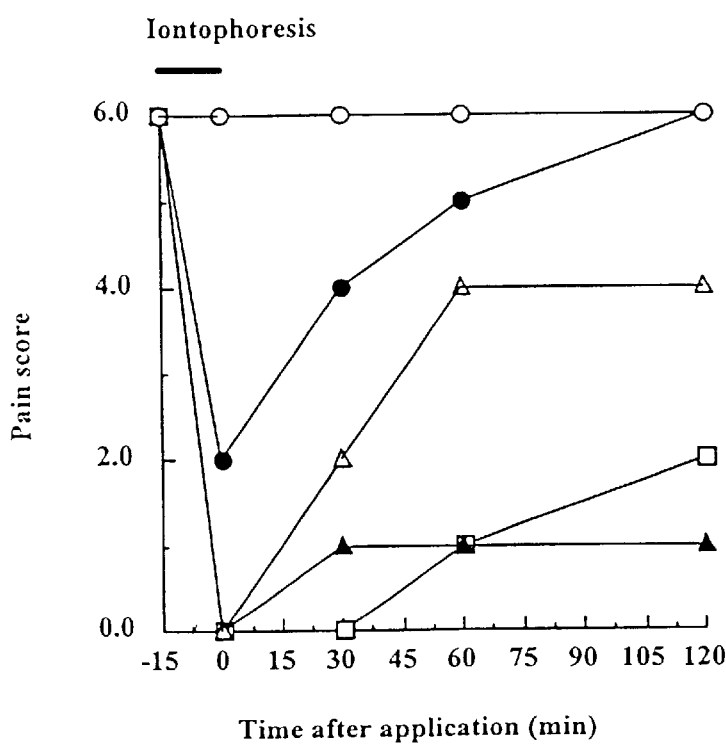
FIG. 13B is a graph for Comparative Example 1 thereon.

FIG. 13A is a graph showing a result for Test Example 5 on Example 1, and FIG. 13B is a graph on Comparative Example 1. In the present graph, the symbol "603" indicates score status of injured skins (electrode structure 1), the symbol "●" indicates score status of injured skins (electrode structure 2), the symbol "Δ" indicates score status of injured skins (electrode structure 3), the symbol "▲" indicates score status of injured skins (electrode structure 4), and the symbol "□" indicates score status of injured skins (electrode structure 5), respectively. As shown in the graph, in Comparison Example 1, the effect of anesthesia was observed in accordance with levels of injury. That is, the biased effect of anesthesia appeared due to the currents being concentrated more into the regions where the level of injury was greater. On the other hand, in Example 1 all painlessness or a state was obtained immediately after completion of energization, and thereafter, the effect of anesthesia decreased gradually. Since not all skins at the regions to be applied have the same impedance, in the case where differently injured skins coexist as in Example 1 as well, it is useful to be able to make the energization homogeneous.

According to the present invention, a handling-convenient device for iontophoresis can be obtained, which can supply a good quantity of current at the same time for each spotted portion suffering from disease.

What is claimed is:

1. A device for iontophoresis comprising:
   a power source apparatus comprising:
      a plurality of output terminals outputting currents of predetermined values, and
      a plurality of current control circuits, each of the output terminals being separately conductively connected to a current control circuit, so as to control current flow to each output terminal independently and simultaneously; and
      a plurality of connecting cords, each cord being connected with one of the output terminals of the power source apparatus at one end thereof and being connected with an electrode structure at an opposing end.

2. The device for iontophoresis according to claim 1, wherein the opposing ends of the connecting cords are connected with said electrode structure in an attachable/detachable fashion.

3. A device for iontophoresis according to claim 1, wherein one end of one of the connecting cords is connected with one of the output terminals of the power source apparatus in an attachable/detachable fashion.

4. The device for iontophoresis according to claim 3, wherein the power source apparatus includes a voltage adjusting circuit adjusting an output voltage in accordance with an output current value.

5. The device for iontophoresis according to claim 3, wherein the opposing ends of the connecting cords are connected with said electrode structure in an attachable/detachable fashion.

6. The device for iontophoresis according to claim 1, wherein the power source apparatus includes a voltage adjusting circuit for adjusting an output voltage in accordance with an output current value.

7. The device for iontophoresis according to claim 6, wherein the opposing ends of the connecting cords are connected with said electrode structure in an attachable/detachable fashion.

8. A device for iontophoresis comprising:
a power source apparatus having a plurality of output terminals outputting currents of predetermined values adjusted by a plurality of current control circuits, respectively; and
a connecting cord portion having a base coupled to the power source apparatus in an attachable/detachable fashion, a plurality of input terminals disposed on the base corresponding to each of the output terminals of the power source apparatus, and a plurality of connecting cords, each cord being connected with one of the output terminals of the power source apparatus at one end thereof and being connected with an electrode structure at the other end.

9. A device for iontophoresis according to claim 8, wherein the power source apparatus includes a voltage adjusting circuit adjusting an output voltage in accordance with an output current value.

10. A device for iontophoresis according to claim 8, wherein the other ends of the connecting cords are connected with said electrode structure in an attachable/detachable fashion.

11. The device for iontophoresis according to claim 8, wherein one end of the connecting cords are connected with the input terminals on the base in an attachable/detachable fashion.

12. A device for iontophoresis according to claim 11, wherein the power source apparatus includes a voltage adjusting circuit adjusting an output voltage in accordance with an output current value.

13. A device for iontophoresis according to claim 11, wherein the other ends of the connecting cords are connected with said electrode structure in an attachable/detachable fashion.

* * * * *